(12) United States Patent
Huo

(10) Patent No.: US 6,835,835 B1
(45) Date of Patent: Dec. 28, 2004

(54) SYNTHESIS FOR ORGANOMETALLIC CYCLOMETALLATED TRANSITION METAL COMPLEXES

(75) Inventor: Shouquan Huo, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/729,207

(22) Filed: Dec. 5, 2003

(51) Int. Cl.⁷ .......................... C07F 15/00; C07F 11/00; C07F 13/00
(52) U.S. Cl. .................. 546/4; 548/402; 556/46; 556/58; 556/137; 428/690
(58) Field of Search .............. 546/4; 548/402; 556/58, 46, 137; 428/690

(56) References Cited

U.S. PATENT DOCUMENTS

| | | | |
|---|---|---|---|
| 2002/0190250 A1 | 12/2002 | Grushin et al. | 257/40 |
| 2003/0068526 A1 | 4/2003 | Kamatani et al. | 428/690 |
| 2003/0096138 A1 * | 5/2003 | Lecloux et al. | 428/690 |

FOREIGN PATENT DOCUMENTS

| WO | WO 00/57676 | 9/2000 |
|---|---|---|

OTHER PUBLICATIONS

L. Chassot, et al. "cis–bis(2–phenylpyridine)platinum(II) (CBPPP): A Simple Molecular Platinum Compound", Inorg. Chem. 1984, 23, pp. 4249–4253.

P. Jolliet, et al., "Cyclometalated Complexes of Palladium(II) and Platinum(II): cis–Configured Homoleptic and Heteroleptic Compounds with Aromatic C N Ligands", Inorg. Chem. 1996, 35, pp. 4883–4888.

S. Lamansky, et al., "Synthesis and Characterization of Phosphorescent Cyclometalated Iridium Complexes", Inorg. Chem., 2001, 40, pp. 1704–1711.

A. Tamayo, et al., "Synthesis and Characterization of Facial and Meridional Tris–cyclometalated Iridium(III) Complexes", J. Am. Chem. Soc., 2003, 125, pp. 7377–7387.

* cited by examiner

*Primary Examiner*—Porfirio Nazario-Gonzalez
(74) *Attorney, Agent, or Firm*—Arthur E. Kluegel

(57) ABSTRACT

The invention provides a process for forming an organometallic cyclometallated complex comprising the step of reacting, in an aprotic organic solvent, an organozinc complex of a desired organic ligand with a metal complex of an element of atomic number 74 to 79 bearing a leaving group.

26 Claims, No Drawings

SYNTHESIS FOR ORGANOMETALLIC CYCLOMETALLATED TRANSITION METAL COMPLEXES

FIELD OF THE INVENTION

This invention relates to the field of organometallic syntheses and to a process for forming organometallic cyclometallated complexes of transition metals comprising the step of reacting an organozinc complex of a desired organic ligand with a metal complex of an element bearing a leaving group to form the corresponding cyclometallated compound.

BACKGROUND OF THE INVENTION

Organometallic cyclometallated complexes of third-row transition metals (e.g. iridium, platinum) have become useful materials and have necessitated synthetic methods for preparing them. Lamasky et al., *Inorg. Chem.*, 2001, 40, 1704–1711, react a bis-cyclometallated iridium complex with excess amount ligand to form a tris complex. However, this method leads to a mixture of isomers in some cases. Tamayo et al., *J. Am. Chem. Soc.* 2003, 125, 7377–7387, reported an improved method to form a pure meridianal isomer of a tris iridium complex. However, the procedure is inconvenient and necessitates finding exact conditions for the reaction of each substrate and therefore is not generally applicable. Furthermore, an efficient and general method for the preparation of mixed tris-cyclometallated iridium complexes has not been developed yet. Grushin et al, U.S. 2002/0190250 A1, reported that the reaction of the trifluoroacetate intermediate of a bis-cyclometallated iridium complex, which was prepared in two steps, with a third ligand produced a meridianal mixed tris-cyclometallated iridium complex, however, no information on isomeric purity was given. A similar method involving the reaction of a bis-cyclometallated iridium compound with a third ligand in glycerol at 180° C. was reported to give a mixed cyclometallated iridium complex (U.S. 2003/0068526 A1). However, we repeated the same reaction and found that a mixture of a series of homoleptic and heteroleptic tris-cyclometallated iridium complexes was formed.

Chassot et al., *Inorg. Chem.*, 1984, 23, 4249–4253, have prepared cyclometallated complexes of platinum by reacting a lithiated ligand with trans-dichlorobis(diethylsulfide) platinum. Jolliet et al., *Inorg. Chem.*, 1996, 35, 4883–4888, also used lithiated ligands to form cyclometallated complexes of the ligands with platinum or palladium, and Lamansky and Thompson, in International Patent Application WO 00/57676, used the same procedure for the preparation of cyclometallated transition metal complexes. These procedures suffer from low yields, as well as the relative instability of and difficulty in handling lithiated organic materials.

It is a problem to be solved to provide a process for the synthesis of organometallic cyclometallated complexes of transition metals that is convenient and generally applicable, is versatile, can be used with a variety of transition metals, and provides high yields, purity, and good control over isomer formation.

SUMMARY OF THE INVENTION

The invention provides a process for forming an organometallic cyclometallated complex comprising the step of reacting, in an aprotic organic solvent, an organozinc complex of a desired organic ligand with a metal complex of an element of atomic number 74 to 79 bearing a leaving group. The process forms the corresponding cyclometallated compound. The process is versatile and provides high yield and pure isomers of cyclometallated compounds of transition metals. It can be used to prepare complexes of mixed ligands, can be used with a variety of transition metals, and can utilize solvents that cannot be used with lithiated ligands.

DETAILED DESCRIPTION OF THE INVENTION

The invention process is summarized above. The process is useful for synthesizing organometallic cyclometallated complexes comprising the step of reacting an organozinc complex of a desired organic ligand with a metal complex bearing a leaving group to form the corresponding cyclometallated compound in the presence of a solvent.

The organozinc complex is represented by Formula 1 or 2:

where:

Y can be an anion such as chloride, fluoride, bromide, iodide, methoxide, acetate, acetylacetate, or trifluoromethanesulfonate; and R is a monoanionic ligand that can be coordinated to a metal through a carbon and a heteroatom and that is capable of replacing X in formula 3.

The carbon may be an $sp^2$ or $sp^3$ carbon. Conveniently, R can be a material that includes an aromatic ring and a heterocyclic ring that may or may not be aromatic. Desirably, the heterocyclic ring can include a nitrogen for coordinating to a metal. Some examples of organozinc complex that include ligands R and can be useful in this method include:

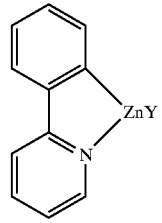

1a

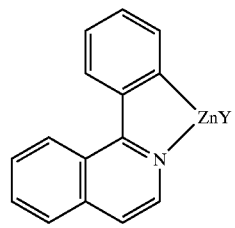

1b

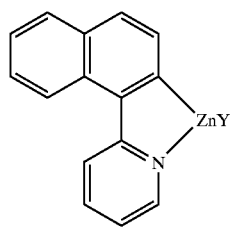
1c
1d
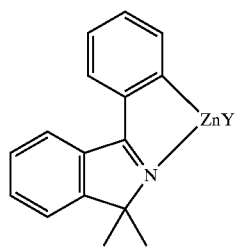
1e
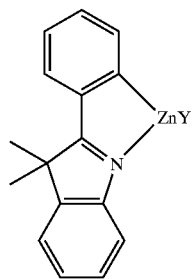
1f
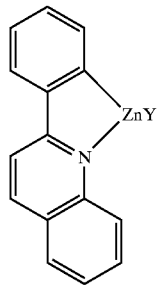
1g
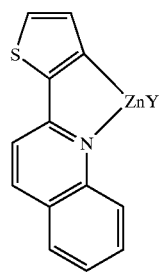
1h
1i
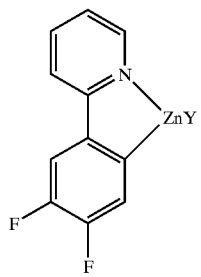
1j
1k
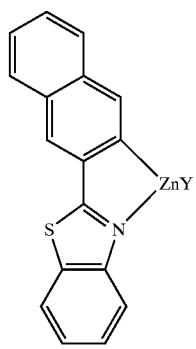
1l
1m
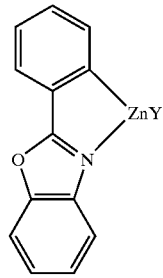
1n

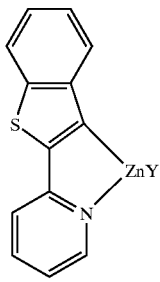

1o

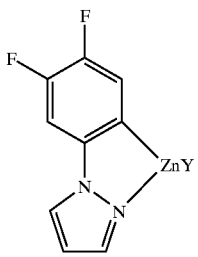

1p

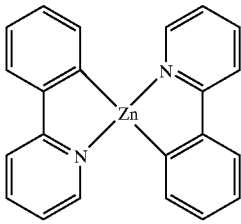

2a

The organozinc complex can be prepared by well-known methods. For example, an alkyllithium compound, aryllithium compound, or alkyl or aryl Grignard reagent can react with a zinc salt via a transmetallation reaction to form the desired organozinc complex (Negishi et al., *J. Org. Chem.*, 1977, 4, 1821). Alternatively, an alkyl halide or aryl halide can react with zinc metal to form the desired organozinc complex via an oxidative zinc insertion reaction (Zhu et al., *J. Org. Chem.*, 1991, 56, 1445).

The metal complex bearing a leaving group includes a transition element of atomic number 74 to 79, that is, selected from the group of tungsten, rhenium, osmium, iridium platinum, and gold. Conveniently, the transition element can be iridium (Ir) or platinum (Pt).

The metal complex can include from 1 to 6 leaving groups which may be any group capable of being replaced by the R of the zinc complex. The number of leaving groups will depend on the coordination state of the chosen metal (e.g. Pt. which preferably forms square-planar complexes, will accommodate from 1 to 4 leaving groups, while Ir, which forms octahedral complexes, will accommodate from 1 to 6 leaving groups) and on the nature of the leaving groups (e.g. monodentate, bidentate). The leaving groups can be monodentate or bidentate, and can be neutral or bear a –1 charge. The metal complex can include a mixture of leaving groups. The metal complex can further include other cyclometallating ligands, provided that sufficient leaving groups remain to allow substitution of at least one more cyclometallating ligand. Useful leaving groups with a –1 charge can include chloride, bromide, iodide, fluoride, acetate, acetonylacetate, trifluoromethanesulfonate, and methoxide. Useful neutral leaving groups include pyridine, diethyl sulfide, diethyl ether, dimethylsulfoxide, and tetrahydrofuran.

The metal complex is represented as Formula 3:

$$L_mMX_n \qquad 3$$

where:

M represents a transition metal of atomic number from 74 to 79;

L represents a cyclometallating ligand;

m is 0, 1, or 2;

X represents a leaving group as described above; and n is from 1 to 6, provided that when n is 2 or more, each X is not necessarily identical. For example, if n is 4, two leaving groups can be chloride and two can be diethyl sulfide.

Some examples of metal complexes that can be used in this process include:

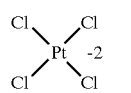

3a

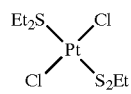

3b

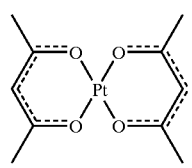

3c

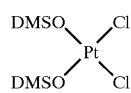

3d

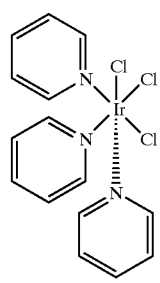

3e

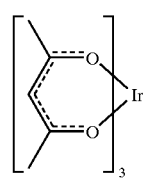

3f

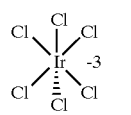

3g

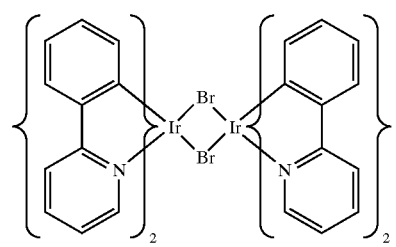

3h

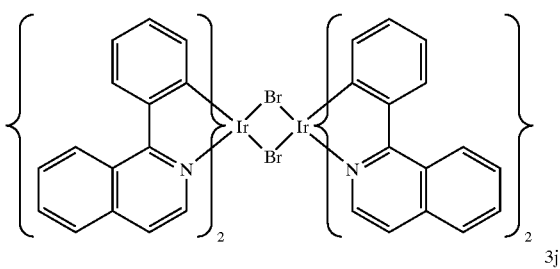

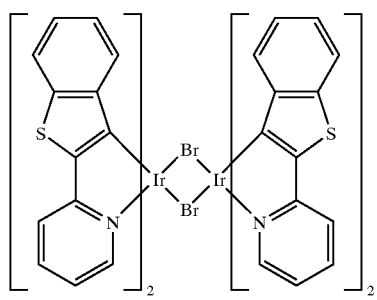

The starting metal complex can be prepared by known methods or can be commercially available. For example, a halogen bridged bis-cyclometallated iridium complexes can be readily prepared in high yields by reacting $K_3IrBr_6$ or any other type of iridium halide salt with the corresponding cyclometallating ligands according to literature procedure, see Nonoyama, *Bull. Chem. Soc. Jpn.,* 1974, 47, 767–768; S.Sprouse et al, *J. Am. Chem. Soc.* 1984, 106, 6647–6653.

Theoretically, the amount of the organozinc complex used, relative to the starting intermediate metal complex as per formula 3, can range from 0.5 to 3 equivalents depending upon the degree of desired substitution. The exact stoichiometry of the reaction will depend upon the nature of the starting materials and the degree of desired ligand substitution, as shown by the following example reactions. In some cases where desired, an excess amount (>3 equivalents) of organozinc complexes can be used to drive the reaction to completion. Representative examples of substitution reactions are listed below but not limited by them.

2 $RZnCl+L_2IrBr_2IrL_2 \rightarrow 2\ L_2IrR+2\ ZnClBr$

3 $RZnCl+K_3IrCl_6 \rightarrow IrR_3+3\ ZnCl_2+3\ KCl$ $RZnCl+Ir(acac)_3 \rightarrow RIr(acac)_2+Zn(acac)Cl$ $RZnCl+Ir(py)_3Cl_3 \rightarrow RIr(py)_2Cl_2+ZnCl_2$ $2RZnCl+Pt(DMSO)_2Cl_2 \rightarrow PtR_2+2ZnCl_2+2\ DMSO$ $R_2Zn+PtCl_2(SEt_2)_2 \rightarrow PtR_2+ZnCl_2+2\ SEt_2$ Under the reaction conditions stated above, the temperature needed to effect formation of the cyclometallated complex can be adjusted in a broad range, typically from 0° C. to room temperature or higher. The temperature requirements are dictated by the nature of the substituents described in Formulas 1, 2, and 3, the reaction types shown above, and other factors. The reaction should be performed under a dry inert atmosphere (e.g. nitrogen, argon).

The reaction is conveniently performed in a solvent to lower viscosity of the mixture. The solvent is an aprotic organic solvent and may be one that evaporates off during the reaction, or it may remain. Suitably, the solvent can be an ether (e.g. diethyl ether, tetrahydrofuran), an alkyl halide (e.g. methylene chloride, 1,2-dichloroethane), a polar aprotic solvent (e.g. dimethylformamide, dimethylacetamide, dimethylsulfoxide), a ketone (e.g. acetone, methyl ethyl ketone), or a nitrile (e.g. acetonitrile). Conveniently, the solvent is tetrahydrofuran, methylene chloride, or a mixture of the two. The solvent should be substantially free of moisture (e.g. Aldrich anhydrous tetrahydrofuran, certified to have less than 0.005% $H_2O$). The reaction mixture can be heterogeneous at the start and can require stirring.

Cyclometallated complexes of the type produced by this invention can have a variety of isomeric forms. For example, tris(2-(phenyl)pyridinato, N,$C^{2'}$)iridium(III) can have two isomeric forms, the facial and the meridianal isomer and bis-(2-(phenyl)pyridinato) N,$C^{2'}$)platinum(II) can have the trans or cis isomers.

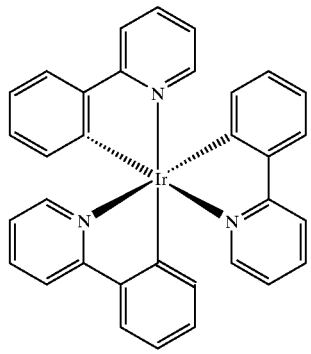

facial

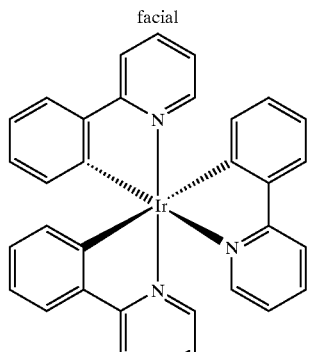

meridianal

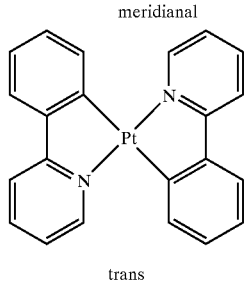

trans

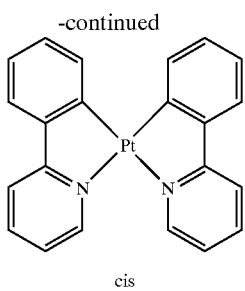

cis

This invention gives good control in the formation of isomers, and frequently produces a single isomer in the case where two or more are possible. It is sometimes desirable to form a different isomer than the one produced in this reaction. Therefore, this invention can be used with methods for interconverting isomers, for example as described by Tamayo et al., above.

Synthesis of Cyclometallated Complexes

The scheme of the overall cyclometallated complex synthesis is exemplified in the following steps to prepare mer-(ppy)$_3$Ir and mer-(piq)Ir(ppy)$_2$. This invention is directed toward Step 3, but it is useful to understand some of the other steps that can be used to synthesize the cyclometallated complexes.

Preparation of mer-(ppy)$_3$Ir
Step 1: Preparation of (ppy)$_2$Ir(μ-Br)$_2$Ir(ppy)$_2$

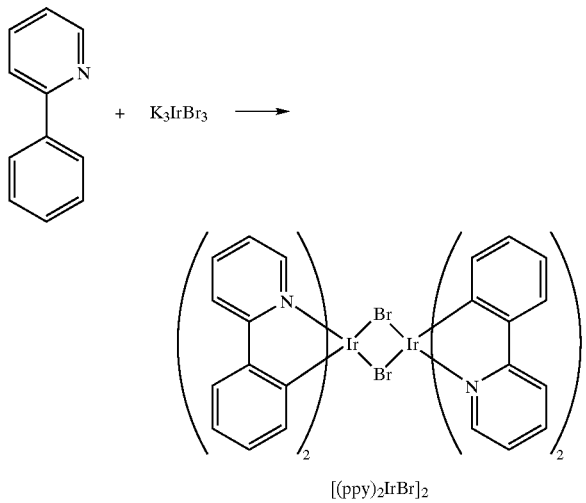

[(ppy)$_2$IrBr]$_2$

Step 2: Preparation of 2-(2-bromophenyl)pyridine

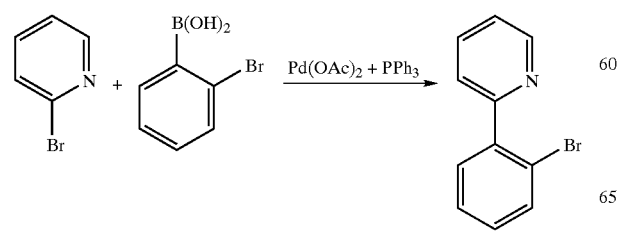

Step 3: Preparation of mer-(ppy)$_3$Ir

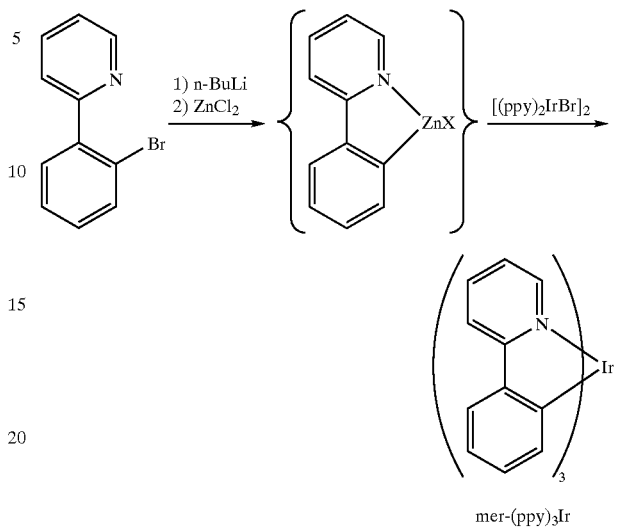

mer-(ppy)$_3$Ir

The process centers around the reaction of organozinc complex with the metal complex to form the organometallic cyclometallated complex (in this case, mer-(ppy)$_3$Ir). The formation of an organozinc complex (in this case, 2-phenylpyridinato-N,C$^{2'}$-zinc(II)) can be attained by reaction of a zinc halide with an organolithium compound (which can be prepared by well-known methods and in some cases are commercially available) or with a Grignard reagent (which can be prepared by methods well-known to those skilled in the art) in Step 3. An additional step, which is not required in all cases, is the conversion of an available metal complex bearing a leaving group into a convenient complex (in this case, (ppy)$_2$Ir(μ-Br)$_2$Ir(ppy)$_2$).. The organometallic cyclometallated complex can be converted to a different isomer. The following schemes show some non-limiting variations on the basic process with different but analogous materials. Steps that are the same as those in another scheme have been omitted for clarity. It will be understood that further substitution is possible.

Preparation of mer-(piq)Ir(ppy)$_2$
Step 2: Preparation of 1-(2-bromophenyl)isoquinoline

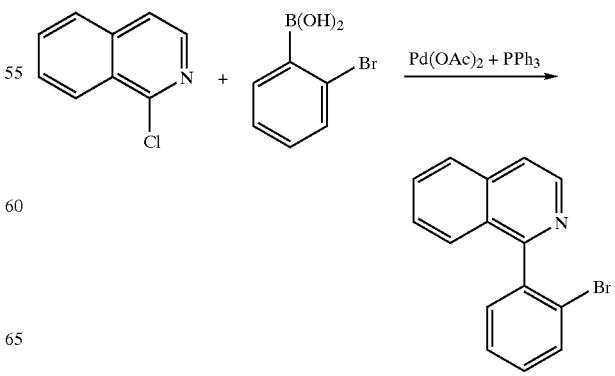

Step 3: Preparation of mer-(piq)Ir(ppy)₂
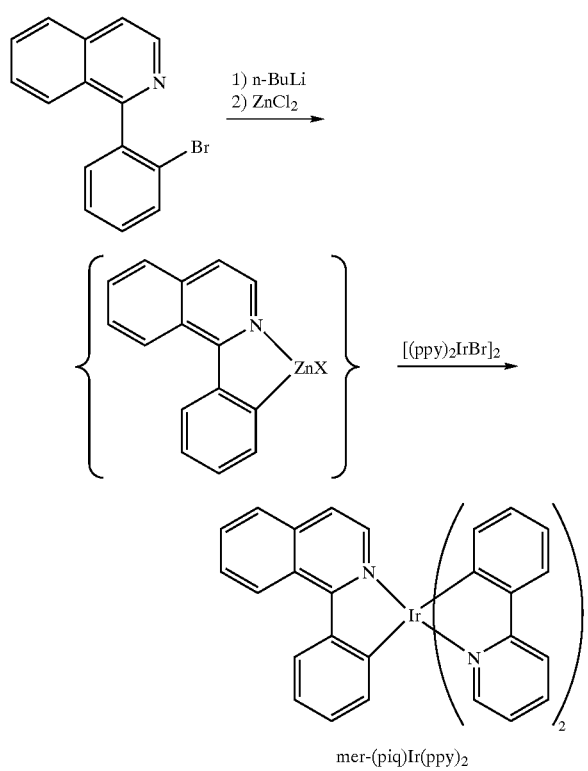
Preparation of mer-(piq)₂Ir(ppy) and fac-(piq)₂Ir(ppy)
Step 3: Preparation of mer-(piq)₂Ir(ppy)
Step 4: Isomerization of mer-(piq)₂Ir(ppy) to fac-(piq₂)Ir(ppy)
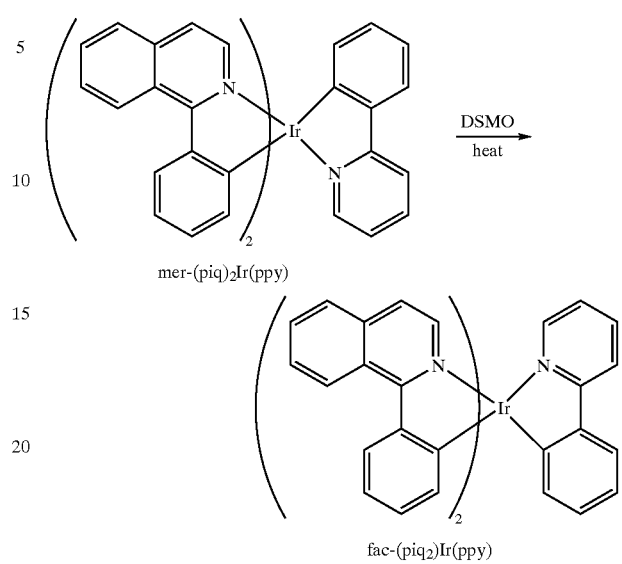
Preparation of mer-(piq)₃Ir
Step 3: Preparation of mer-(piq)₃Ir(ppy)₂
Preparation of Pt(piq)₂
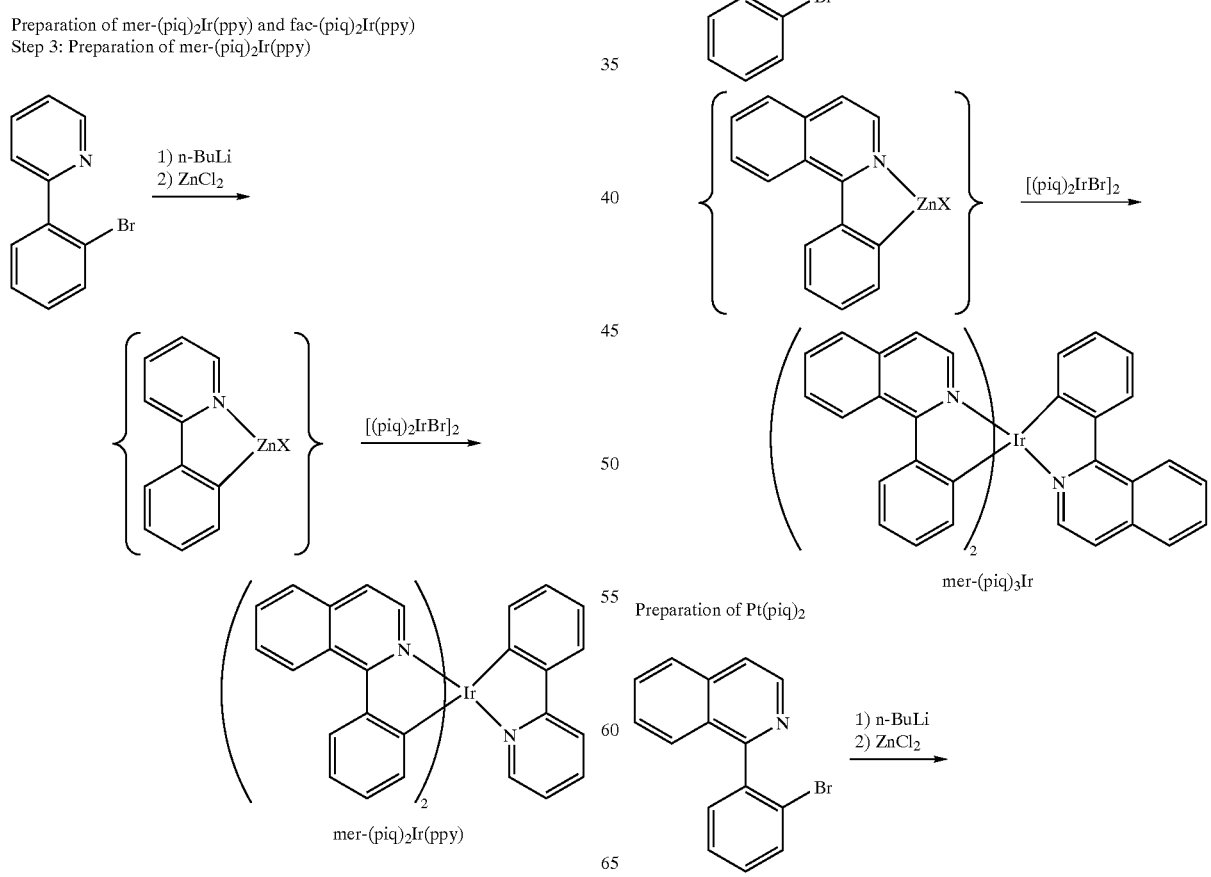

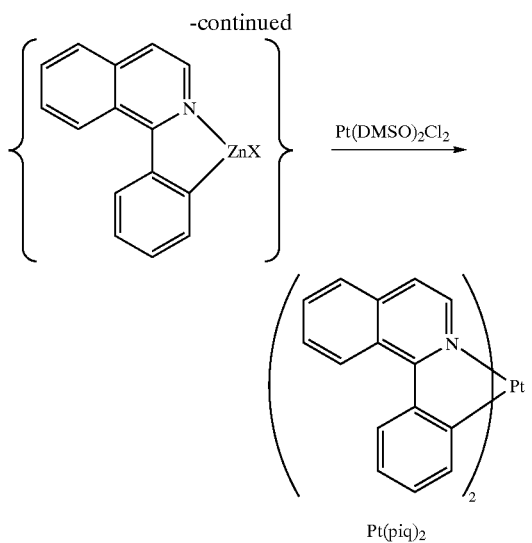

Pt(piq)₂

Unless otherwise specifically stated, use of the term "group", "substituted" or "substituent" means any group or radical other than hydrogen. Additionally, when reference is made in this application to a compound or group that contains a substitutable hydrogen, it is also intended to encompass not only the unsubstituted form, but also its form further substituted with any substituent group or groups as herein mentioned, so long as the substituent does not destroy properties necessary for the intended utility. Suitably, a substituent group may be halogen or may be bonded to the remainder of the molecule by an atom of carbon, silicon, oxygen, nitrogen, phosphorous, or sulfur. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, cyclohexyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, hydrophobic groups, solubilizing groups, blocking groups, and releasing or releasable groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

EXAMPLES

Preparation of 2-(2-bromophenyl)pyridine

To a 250 mL flask were charged 2-bromopyridine (4.8 mL, 49 mmol), 2-bromophenylboronic acid (9.85 g, 49 mmol), triphenylphosphine (1.09 g, 4.17 mmol), and ethylene glycol dimethyl ether (55 mL). A homogeneous solution was formed. To this solution was added 2 M $K_2CO_3$ (60 mL, 120 mmol). The mixture was purged with nitrogen then $Pd(OAc)_2$ (0.24 g, 1 mmol) was added. The mixture was refluxed for 5 h then cooled to room temperature. The reaction mixture was transferred into a separating funnel and the organic layer was separated and retained. The aqueous phase was extracted with ethyl acetate (EtOAc) (4×100 mL). The combined organic layers were washed with water (200 mL) and brine (200 mL) and dried over $MgSO_4$. Filtration and evaporation produced a dark brown oil, which was purified by chromatography on silica gel with $CH_2Cl_2$:heptane=2:1 and $CH_2Cl_2$ to provide a light yellow oil, 7.57 g, 65%.

Preparation of 1-(2-bromophenyl)isoquinoline

The same procedure described above was used for the synthesis of this compound starting with 1-chloroisoquinoline. The compound was purified by chromatography on silica gel with $CH_2Cl_2$-EtOAc=97:3, 85.7%.

$L_2Ir(\mu\text{-Br})_2IrL_2$ complexes were prepared from $K_3IrBr_6$ or any other iridium halide salts and the appropriate ligand according to literature procedures (S. Sprouse et al, *J. Am. Chem. Soc.* 1984, 106, 6647–6653)

Preparation of $[Ir(ppy)_2Br]_2$

A solution of $K_3IrBr_6$ (4.44 g, 5.63 mmol) and 2-phenylpyridine (2.41 mL, 16.8 mmol) in 2-methoxethanol (150 mL) and water (50 mL) was refluxed under nitrogen for 20 hours. The mixture was cooled to room temperature and yellow precipitates were collected on a glass frit by filtration and washed with 95% ethanol and acetone. The crude product was dissolved in 400 mL of dichloromethane and filtered. The filtrate was concentrated while toluene (125 mL) and hexanes (50 mL) were added in two portions. The final volume was ca. 250 mL. After cooling to room temperature, the yellow precipitate was collected by filtration and washed with toluene and heptane and dried. The product was obtained as bright yellow powder, 2.66 g, 81%.

Preparation of mer-$(ppy)_3Ir$. Representative Procedure

To a solution of 2-(2-bromophenyl)pyridine (0.48 g, 2 mmol) in THF (10 mL) cooled with a dry ice-acetone bath was added dropwise a solution of n-BuLi in hexanes (1.3 mL, 1.6 M, 2.08 mmol, Aldrich) via a syringe. After the reaction mixture was stirred at −78° C. for 30 min, a solution of $ZnCl_2$ in ether (2 mL, 1.0 M, 2 mmol, Aldrich) was added slowly via a syringe. The cooling bath was removed and the reaction mixture was warmed to ca 0° C. to room temperature. The bromide-bridged dimer $[Ir(ppy)_2Br]_2$ (0.58 g, 0.5 mmol) was added to the reaction mixture in one portion and the mixture was stirred for 30 min. Dichloromethane (10 mL) was added to accelerate the reaction. After stirring for ca. 1 hour at room temperature, the mixture was transferred into a one-necked flask and remaining yellow precipitates were washed into the flask with dichloromethane. The solvent was evaporated and the residue was dissolved in dichloromethane and purified by flash chromatography on silica gel with dichloromethane. The product was obtained as isomerically pure mer-$(ppy)_3Ir$, 0.51 g, 78%.

Preparation of mixed tris-cyclometallated iridium complexes, mer-$(ppy)_2Ir(piq)$ Representative Procedure To a solution of 1-(2-bromophenyl)isoquinoline (1.02 g, 3.59 mmol) in anhydrous THF (15 mL, Aldrich), cooled to −78° C. with a dry ice-acetone bath, was added dropwise a solution of n-BuLi in hexanes (2.24 mL, 1.6 M, 3.6 mmol, Aldrich). The mixture was stirred at −78° C. for 30 min and a solution of $ZnCl_2$ in ether (3.6 mL, 1.0 M, 3.6 mmol, Aldrich) was added slowly via a syringe. The cooling bath was removed and the reaction mixture was warmed to between 0° C. and room temperature. The bromide-bridged dimer $[Ir(ppy)_2Br]_2$ (1.04 g, 0.9 mmol) was added to the reaction mixture in one portion. Dichloromethane (20 mL) was added to accelerate the reaction. After stirring for 3 hour at room temperature, any remaining organozinc reagent was quenched with 5 mL of methanol. The mixture was poured into water (100 mL) and extracted with dichloromethane (3×100 mL). The combined organic layers were washed with water (2×100 mL) and brine (200 mL) and dried over $MgSO_4$. After filtration, the solvents were evaporated and the crude materials were treated with methanol (50 mL) and the product was collected by filtration and washed with methanol (50 mL), yellow orange solids, >98% isomeric purity by HPLC, 1.03 g, 81%.

The organometallic cyclometallated complexes synthesized according to this invention may be incorporated in an emissive layer of an OLED device.

The entire contents of the patents and other publications referred to in this specification are incorporated herein by reference.

What is claimed is:

1. A process for forming an organometallic cyclometallated complex comprising the step of reacting, in an aprotic organic solvent, an organozinc complex of a desired organic ligand with a metal complex of an element of atomic number 74 to 79 bearing a leaving group.

2. The process of claim 1 wherein the element of atomic number 74 to 79 is platinum.

3. The process of claim 1 wherein the element of atomic number 74 to 79 is iridium.

4. The process of claim 1 wherein the ligand is a monoanionic ligand that can be coordinated to a metal through an $SP^2$ carbon and a heteroatom.

5. The process of claim 4 wherein the ligand includes an aromatic ring and a heterocyclic ring.

6. The process of claim 5 wherein the heterocyclic ring includes a nitrogen for coordinating to the metal of the metal complex.

7. The process of claim 6 wherein the ligand includes at least one chosen from among the following:

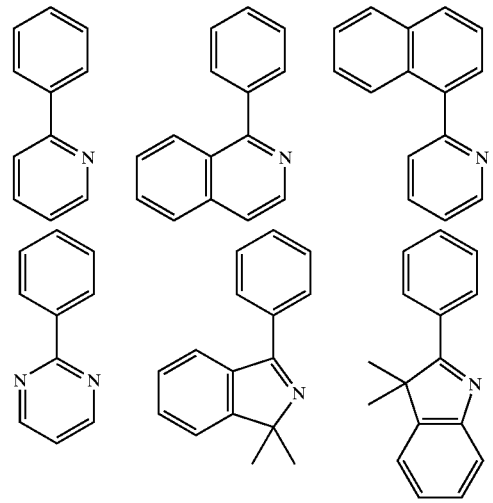

-continued

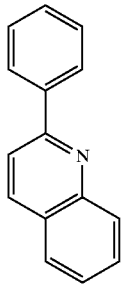

8. The process of claim 1 wherein the solvent comprises an ether, an alkyl halide, a polar aprotic solvent, or a nitrile group.

9. The process of claim 8 wherein the solvent comprises tetrahydrofuran, methylene chloride, or a mixture of the two.

10. The process of claim 8 wherein the solvent is substantially free of water.

11. The process of claim 1 wherein the metal complex includes from 1 to 6 leaving groups.

12. The process of claim 11 wherein one or more of the leaving groups are monodentate.

13. The process of claim 11 wherein one or more of the leaving groups are bidentate.

14. The process of claim 11 wherein one or more of the leaving groups are neutral.

15. The process of claim 14 wherein the leaving groups include pyridine, diethyl sulfide, diethyl ether, dimethylsulfoxide, or tetrahydrofuran.

16. The process of claim 11 wherein one or more of the leaving groups have a −1 charge.

17. The process of claim 16 wherein the leaving groups include chloride, bromide, iodide, fluoride, acetate, acetonylacetate, trifluoromethanesulfonate, or methoxide.

18. The process of claim 1 wherein the organozinc complex is formed from a zinc salt and an organolithium compound.

19. The process of claim 1 wherein the organozinc complex is formed from a zinc salt and a Grignard reagent.

20. The process of claim 1 wherein the organozinc complex is formed from elemental zinc and an organohalide.

21. The process of claim 1 wherein the reaction is performed at room temperature or higher.

22. The process of claim 1 wherein the reaction is performed under an inert atmosphere.

23. The process of claim 1 wherein a subsequent step converts the resulting isomer into a different isomer.

24. The process of claim 23 wherein the conversion is effected by heat or irradiation.

25. The process of claim 1 wherein the organozinc complex is represented by formula 1 or 2

$$RZnY \qquad 1$$

$$R_2Zn \qquad 2$$

wherein Y is an anion and R is a monoanionic ligand that can be coordinated to a metal through a carbon and a heteroatom.

26. The process of claim 1 wherein the metal complex of an element of atomic number 74 to 79 is represented by Formula 3:

$$L_mMX_n \qquad 3$$

wherein:

M represents a transition metal of atomic number from 74 to 79;

L represents a cyclometallating ligand;

m is 0, 1, or 2;

each X represents an independently selected leaving group; and n is from 1 to 6.

* * * * *